(12) United States Patent
Yahnite (10) Patent No.: US 11,987,101 B2
(45) Date of Patent: May 21, 2024

(54) VEHICLE AIR FRESHENER

(71) Applicant: John Yahnite, Coconut Creek, FL (US)

(72) Inventor: John Yahnite, Coconut Creek, FL (US)

( * ) Notice: Subject to any disclaimer, the term of this patent is extended or adjusted under 35 U.S.C. 154(b) by 660 days.

(21) Appl. No.: 17/212,996

(22) Filed: Mar. 25, 2021

(65) Prior Publication Data

US 2021/0300158 A1  Sep. 30, 2021

Related U.S. Application Data

(60) Provisional application No. 63/000,256, filed on Mar. 26, 2020.

(51) Int. Cl.
*B60H 3/00* (2006.01)
*B60H 1/00* (2006.01)
*B60H 1/22* (2006.01)

(52) U.S. Cl.
CPC ......... *B60H 3/0007* (2013.01); *B60H 1/0025* (2013.01); *B60H 1/00428* (2013.01); *B60H 1/0065* (2013.01); *B60H 1/2215* (2013.01); *B60H 2003/0057* (2013.01)

(58) Field of Classification Search
CPC ... A61L 9/00; A61L 9/01; A61L 9/012; A61L 9/02; A61L 9/03; B60H 1/00; B60H 1/0025; B60H 1/00421; B60H 1/00428; B60H 1/00642; B60H 1/0065; B60H 1/22; B60H 1/2215; B60H 3/00; B60H 3/0007; B60H 3/0014; B60H 3/005; B60H 3/0057
See application file for complete search history.

(56) References Cited

U.S. PATENT DOCUMENTS

| 5,373,581 | A | 12/1994 | Smith |
| 6,805,300 | B2 | 10/2004 | Munroe et al. |
| 7,544,331 | B1 | 6/2009 | Pettaway |
| 8,765,073 | B1 * | 7/2014 | Hsiao ........................ A61L 2/00 239/34 |
| 9,042,712 | B2 | 5/2015 | Irvin et al. |
| 9,522,208 | B2 * | 12/2016 | Esses ...................... A61L 9/032 |
| 2018/0064839 | A1 * | 3/2018 | Hsiao ........................ A61L 9/03 |
| 2018/0228930 | A1 * | 8/2018 | Davis ..................... A61L 9/032 |

* cited by examiner

*Primary Examiner* — Natasha E Young
(74) *Attorney, Agent, or Firm* — Malloy & Malloy, P.L.; Robert M. Downey (57) ABSTRACT

An air freshener device for an automobile includes a housing, a removable vented cover, and an interior chamber containing a fan and a heater. The housing is structured for removable receipt of a wax melt container within an upper portion of the interior chamber. In a preferred embodiment, the wax melt container is at least partially formed of silicone and includes a removable spill-proof vented top. A button control on the housing is operable to electrically power the fan and heater, causing a fragrant wax material in the wax melt container to melt, thereby releasing a pleasant aroma out from the vented cover and within the surrounding atmosphere. The interior chamber may further include one or more LEDs for directing light upwardly and out through the vented cover.

11 Claims, 12 Drawing Sheets

VEHICLE AIR FRESHENER

BACKGROUND OF THE INVENTION

This non-provisional patent application is based on provisional patent application Ser. No. 63/000,256 filed on Mar. 26, 2020.

FIELD OF THE INVENTION

The invention relates to electrically powered air fresheners and, more particularly, to an electrically powered wax melt air freshener for use in automobiles.

DESCRIPTION OF THE RELATED ART

Air fresheners of various types are well-known in the art. Of particular interest to the present invention are electrically powered air fresheners and, more particularly, wax melt air fresheners that are adapted to melt a wax material of a particular scent and to release the scent into the surrounding atmosphere. Currently, wax melt air fresheners are designed for use in a static environment, such as in a home or office, wherein the wax melt air freshener device is placed on a counter or other surface in a location where the device will not be disturbed. This is particularly important because of the danger of melted wax spilling from the device. In these existing wax melt air fresheners, a cube of hardened wax of the desired scent is placed within a melting chamber of the device. Typically, the melting chamber is made of a ceramic material or similar material that is heated by a heating element which causes the wax to melt and release the desired scent. When the device is turned off, the wax eventually hardens and must be scraped out with a tool if it is desired to change the scent of the wax material. In the event the device is abruptly moved or turned from an upright position, any melted wax in the device might leak from the device, potentially causing injury or other damage. For this reason, existing electrically powered wax melt air freshener devices are not suitable for use in automobiles due to the possibility of accidental wax spills. Moreover, the existing electrically powered wax melt devices are not easy to clean due to the nature and structure of the wax melt chamber in these devices.

Accordingly, there remains a definite need for an electrically powered wax melt air freshener device that can be safely used within an automobile, for placement in a cup holder or in another holder device, such as attached to an AC vent in the automobile, and wherein the air freshener device can be electrically powered by simply plugging the air freshener device into a USB connection port or cigarette lighter socket in the automobile. There is a further need for an electrically powered wax melt air freshener device for use in automobiles that is spill proof, thereby preventing melted wax from accidentally leaking or spilling from the device and potentially causing injury or property damage.

SUMMARY OF THE INVENTION

The present invention is directed to an air freshener device and, more particularly, to an electrically powered wax melt air freshener device for use in automobiles. The air freshener device includes a housing and a vented cover that removable attaches to the top of the housing. An interior chamber of the housing contains a fan and a heater. The housing is structured for removable receipt of a wax melt container within an upper portion of the interior chamber so that a bottom of the wax melt container is either in direct contact with the heater or in close proximity to the heater so that a fragrant wax material placed in the wax melt container will melt from exposure to heat generated by the heater. In a preferred embodiment, the wax melt container is at least partially formed of a silicone material and includes a removable spill-proof vented top. A button control on the housing is operable to electrically power the fan and heater, causing the fragrant wax material in the wax melt container to melt, thereby releasing a pleasant aroma out from the vented cover and within the surrounding atmosphere. The interior chamber may further include one or more LEDs for directing light upwardly and out through the vented cover. The LEDs may be adapted for changing color, either as a steady color or constantly changing colors during operation. A power cord for connecting to an electric power source may be either removably attachable to the housing of the air freshener device or permanently attached. In the event the power cord is removably attachable, the connection of the power cord to the housing of the air freshener device may be by any well-known connection means, including a USB connection. An opposite end of the power cord is adapted for connection to a USB port, such as in a automobile, or a cigarette lighter socket. This allows the user to connect to a vehicle's electrical power system for energizing the air freshener device, including the fan, heater and LEDs. The air freshener device can be removed from the user's automobile and used in their home or a hotel room when traveling.

The wax melt container is at least partially formed of silicone to allow for easy removal of the fragrant wax material that has been previously melted and then hardened. In this instance, the user can simply depress the bottom of the silicone wax melt container, causing the bottom to deform which results in the hardened wax material being released from the wax melt container. The silicone material also provides for a cool touch surface to prevent the user from being burned when removing the wax melt container from the housing of the device.

An important feature of the invention is maintaining the melted wax within the device so that the wax does not leak out or spill from the device and cause injury or other damage. To achieve this, a seal is provided between the cover and housing of the air freshener device. Additionally, the vented cover and vent openings on the top of the wax melt container are made to be spill-proof.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENTS

Referring to the several views of the drawings, and initially FIGS. 1, 2-7, the air freshener device of the present invention is shown and is generally indicated as 10 throughout the drawings. The device includes a housing 12 and a cover 14 that removably attaches to a top of the housing. In a preferred embodiment, the cover 14 is attached to the top of the housing 12 by cooperating screw threads including screw threads 16 about an upper exterior portion of the housing and cooperating screw threads 18 on an inner surface of the cover (see FIG. 7). An O-ring or other seal 19 about the top of the housing allows for a sealed, spill-proof attachment of the cover 14 to the housing 12, preventing hot wax inside the air freshener device from leaking out from between the cover and housing 12 in the event the air freshener device is tipped sideways or inverted. The housing 12 includes an interior chamber, including a lower fan chamber 20 and an upper fragrance chamber 22. A transverse shelf 24 separates the lower fan chamber 20 and the upper fragrance chamber 22. The transverse shelf 24 includes openings 26 formed therethrough to allow airflow from the fan chamber, created by fan 50 up through the openings 26 and through the upper fragrance chamber 22, as described in more detail hereinafter. The transverse shelf 24 is transparent to allow light to pass through the transverse shelf 24.

An annular ledge 30 or similar annular top wall is provided at or near the top of the fragrance chamber. The annular ledge 30 is fixed to the side walls of the fragrance chamber and is not removable. The annular ledge 30 has a central opening 31 that is sized, structured and configured for removable and supported receipt of a wax melt container 60 therein. The annular ledge 30 also includes vent openings 34, such as elongated slots, to allow for passage of upward airflow from the fan chamber 20 through the upper fragrance chamber 22 and out through the top annular ledge 30. The top annular ledge 30 may also include light lenses 32 arranged about the entire circumference of the annular ledge 30 for allowing light from LEDs in the lower fan chamber to be directed out through the top of the housing 12 and through the cover 14, as described more fully hereinafter. Alternatively, the annular ledge 30 may be formed of a transparent material or translucent material that allows for passage of light through the annular ledge 30.

Figure 1:
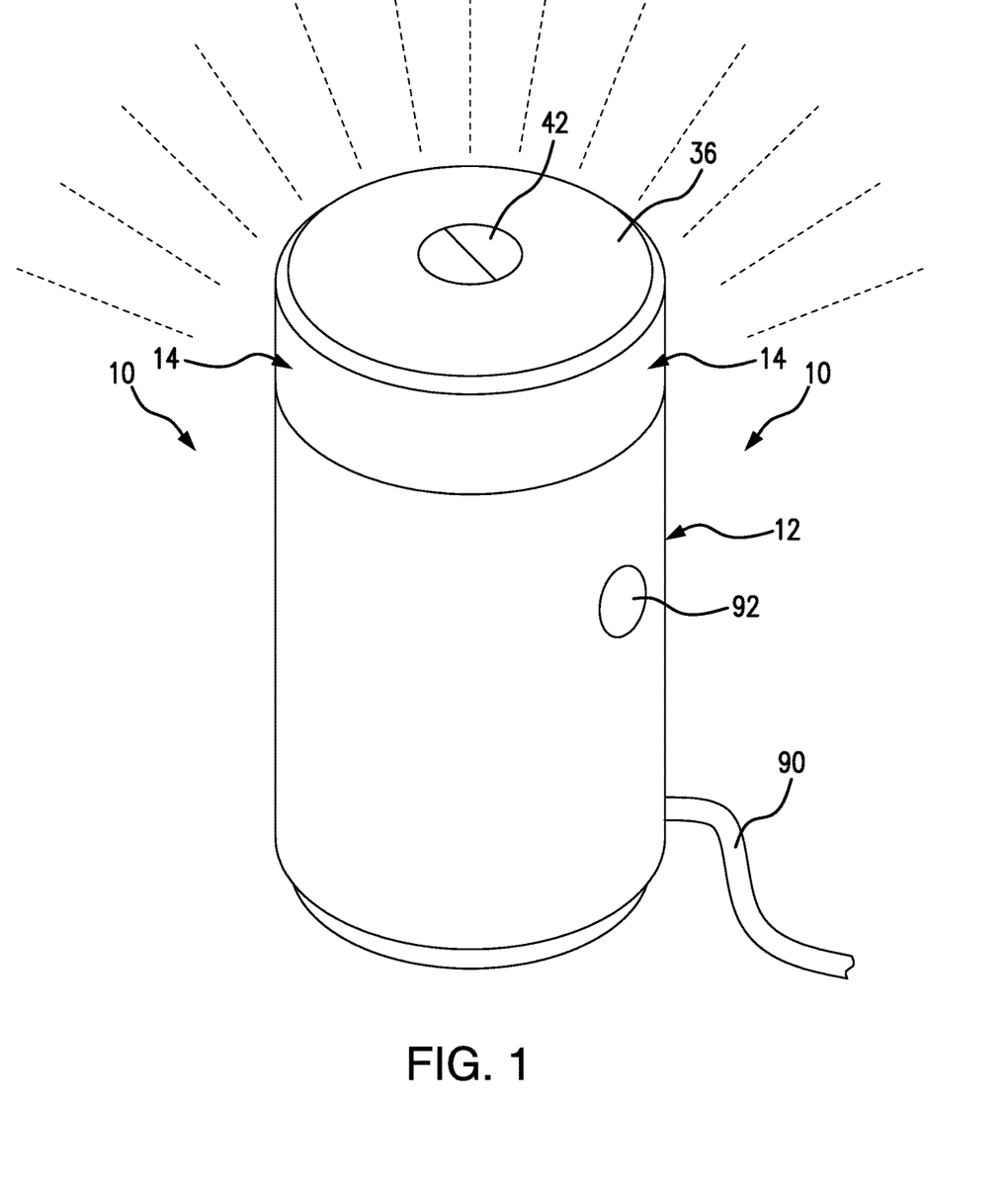
FIG. 1 is a front, top perspective view of the vehicle air freshener device of the present invention, in accordance with one preferred embodiment thereof.
Figure 1A:
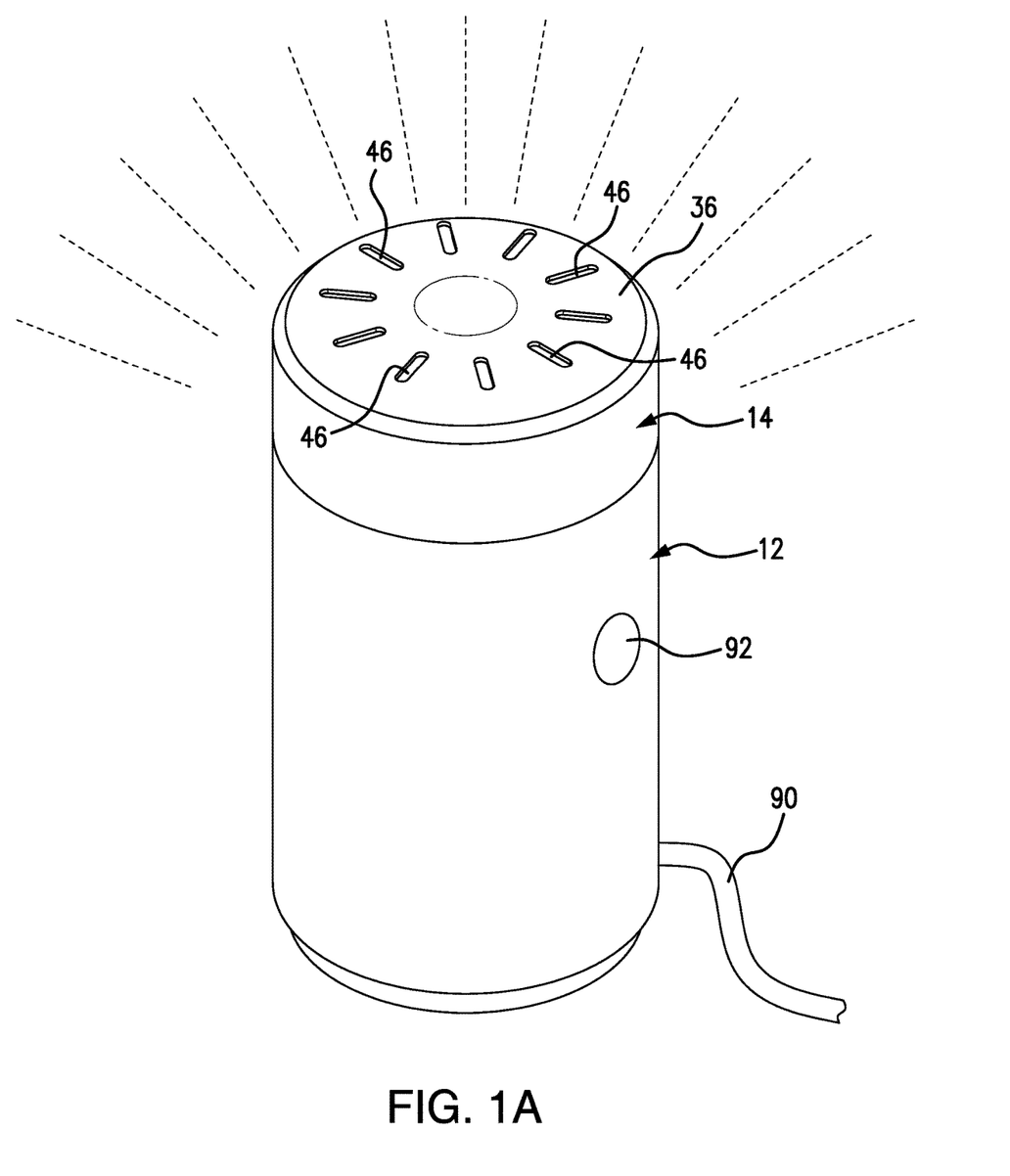
FIG. 1A is a front, top perspective view of the vehicle air freshener device of the present invention in accordance with another preferred embodiment thereof.
Figure 2:
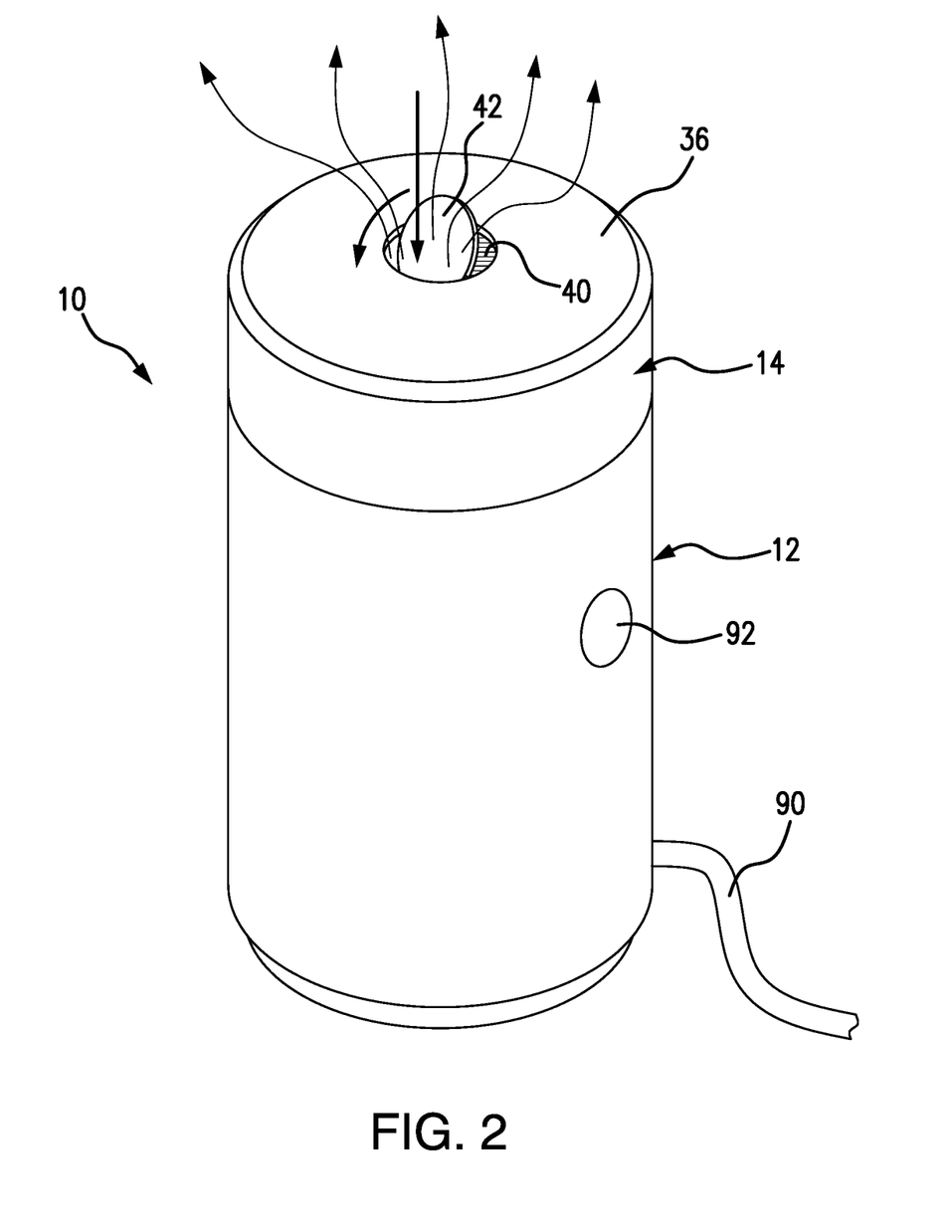
FIG. 2 is a front, top perspective view of the vehicle air freshener device of FIG. 1 showing a top vent on the cover of the device in an open position to release the aroma of the melted fragrant wax during operation of the device.
Figure 3:
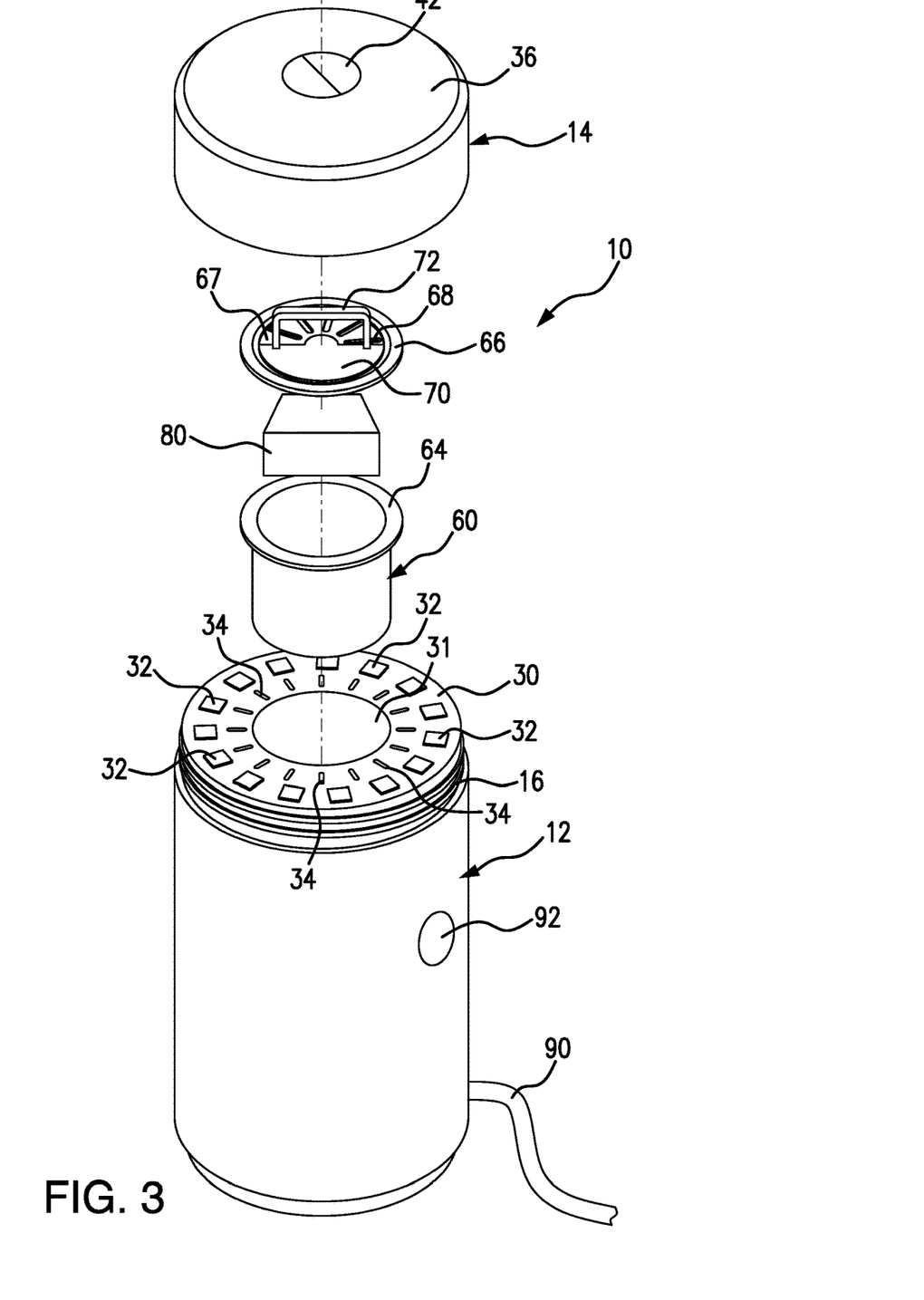
FIG. 3 is a fully exploded perspective view of one preferred embodiment of the vehicle air freshener device of the present invention.
Figure 4:
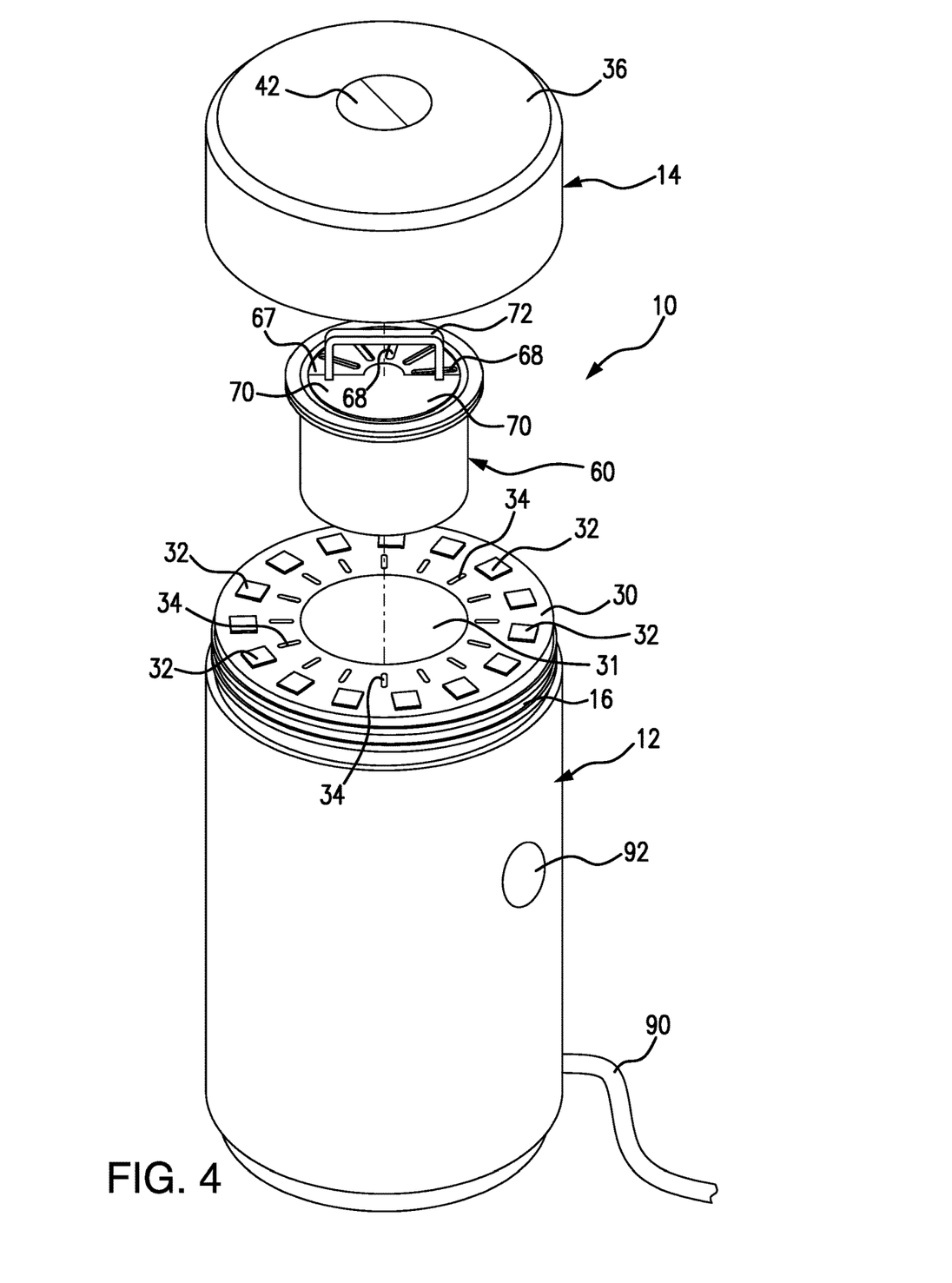
FIG. 4 is a partially exploded perspective view of the vehicle air freshener device of FIG. 3.
Figure 5:
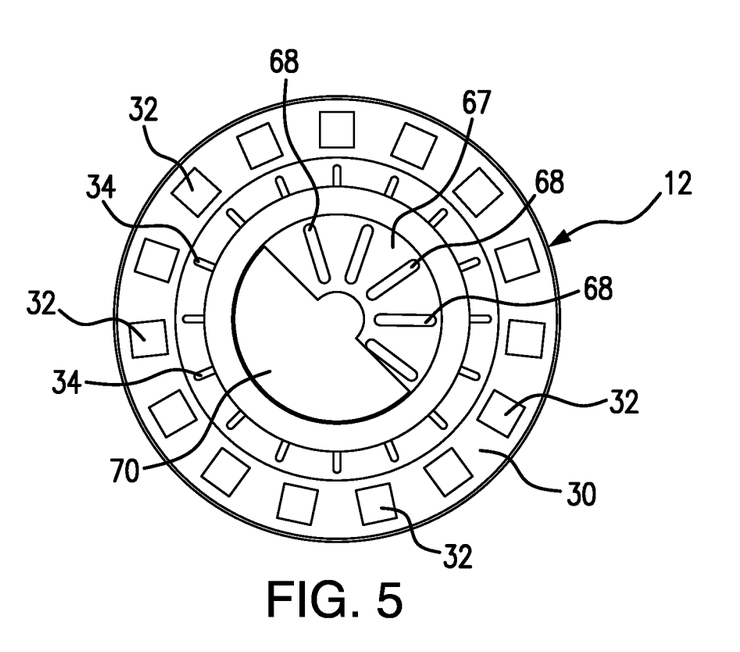
FIG. 5 is a top plan view of the housing of the vehicle air freshener device shown with a wax melt container received within an opening in a top annular ledge on the housing, and wherein the wax melt container has a vented top with the vent in an open position.
Figure 6:
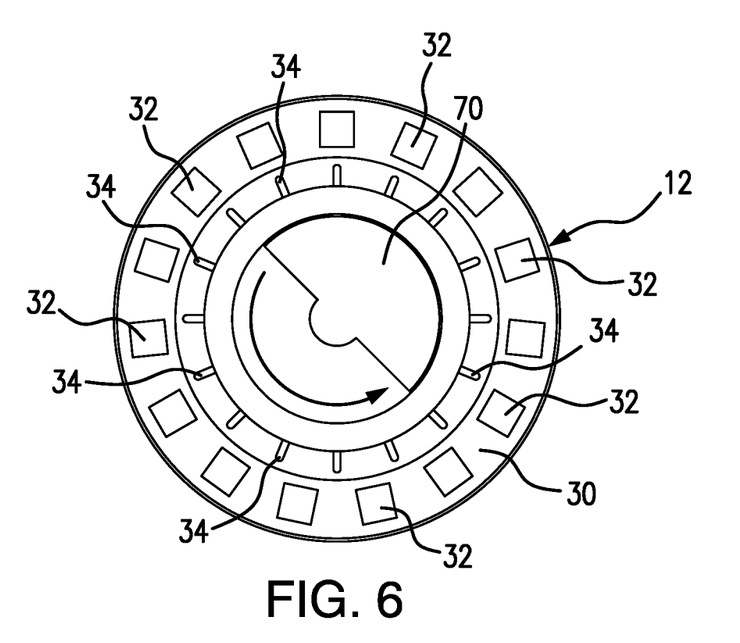
FIG. 6 is a top plan view of the housing of the vehicle air freshener device and wax melt container of FIG. 5 shown with the top vent of the wax melt container in a closed position.
Figure 7:
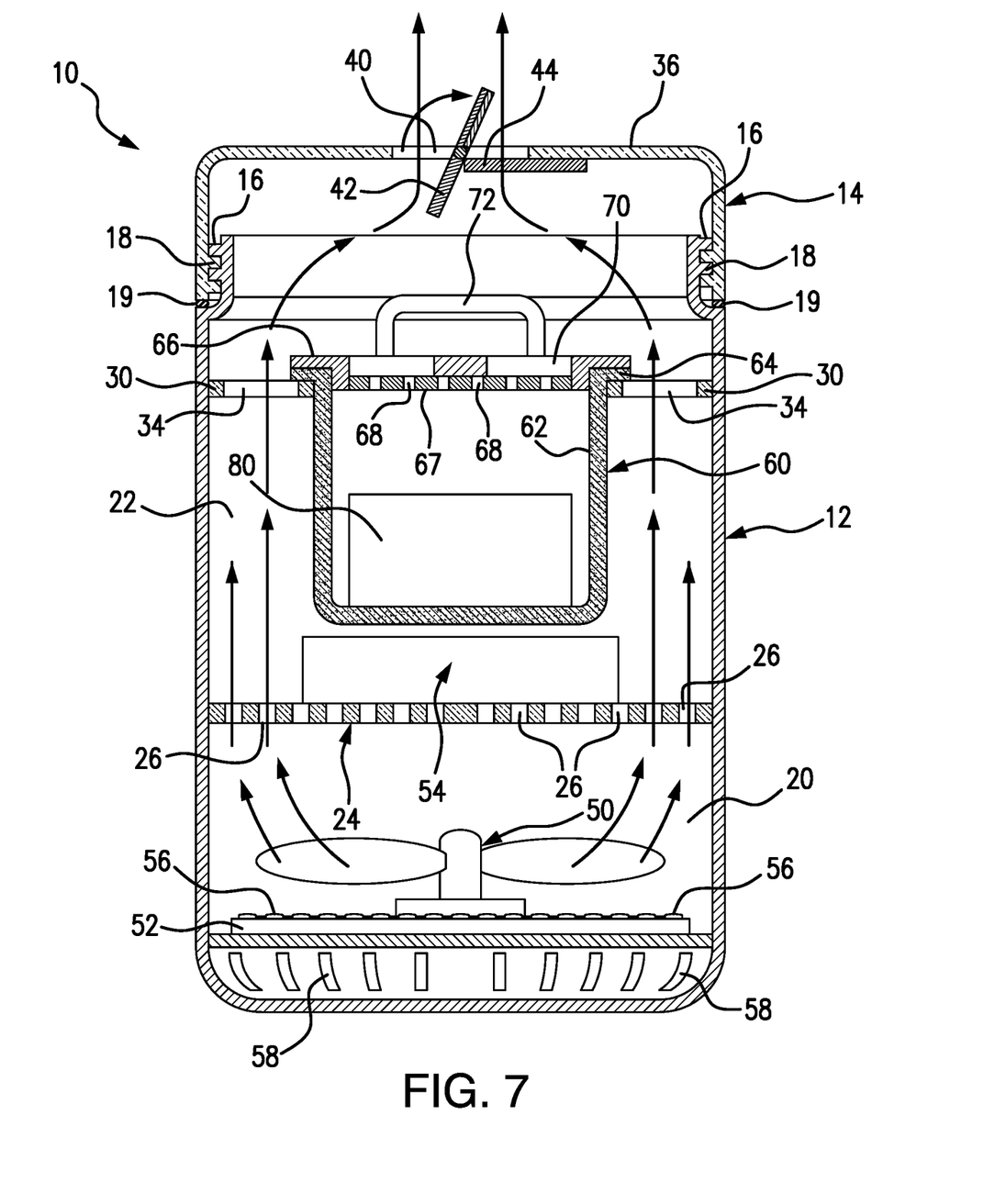
FIG. 7 is a side elevational view of the assembled vehicle air freshener device of FIG. 3, shown in cross-section, and in operational mode for melting a fragrant wax within the wax melt container to thereby release the aroma of the melted fragrant wax material through the vented cover of the device.

As seen throughout the drawing figures, the cover 14 includes a top side 36 that is preferably formed of a transparent or translucent material to allows passage of light therethrough. A central opening 40 in the top allows the airflow from the fan 50 to pass out through the cover 14, carrying an aroma from the fragrant wax 80 that is melted within the wax melt container 60. In one embodiment, the vent opening 40 in the top 36 of the cover 14 includes a circular flap 42 that hinges open and closed, as seen in FIGS. 2-4 and 7. A bottom side of the circular flap may include a magnet or, alternatively, the entire circular flap may be made of a magnetic material, for releasable, magnetic attachment to a magnet 44 mounted to the underside of the cover 14, thereby releasably holding the circular flap 42 in the closed position, as seen in FIGS. 3-4. When the air freshener device 10 is operated, the circular flap 42 may be hinged open, by depressing on the side of the circular flap opposite the magnet 44, thereby opening the central vent 40 to allow release of the airflow and aroma into the surrounding atmosphere of the automobile or other space. The heater 54 within the interior chamber of the housing 12 is supported so that it is positioned directly below the wax melt container 60, as seen in FIG. 7. More particularly, the silicone bottom of the wax melt container 60 may rest against the heater 54 or, alternatively, there may be a small space or gap between the bottom of the silicone wax melt container and the heater 54. In a preferred embodiment, the heater 54 is similar to a warming plate, such as the type used for keeping coffee warm on an automatic drip coffee maker or a desktop coffee cup heater. In this instance, the silicone wax melt container 60 may sit directly on the heater 54. The heater 54 is adapted to heat the fragrant wax material 80 to a temperature that is sufficient to melt the wax and release the desired aroma through the top 66 of the wax melt container. More particularly, the top 66 of the wax melt container 60 may include an annular rim that sits on top of the silicone rim 64 of the wax melt container 60 along with a vent plate 67 that covers the open top of the wax melt container 60. The vent plate 67 includes an arrangement of vented openings 68 therein to allow passage of the fragrance of the melted wax material 80 out through the top 66 of the wax melt container 60. As seen in FIGS. 4-7, the vented openings 68 are preferably elongated slots formed in the vent plate 67. A vent closure mechanism 70 is movable between an open position, as seen in FIG. 5, to expose the elongated slot vent openings 68, thereby allowing release of the aroma of the melting wax material 80. The vent closure mechanism 70 may be moved to the closed position as seen in FIG. 6, to cover the slotted vent openings 68 when the device 10 is turned off, thereby containing the aroma of the wax 80 within the wax melt container 60. A handle 72 on the top 66 of the wax melt container 60 allows for convenient removal and replacement of the wax melt container 60 within the central opening 31 of the annular ledge 30 at the top of the fragrance chamber 22.

The heater 54 is controlled by a thermistor to maintain the temperature of the heater 54 within a desired temperature range that is sufficient to melt the wax 80. This is generally between the range of 100 degrees Fahrenheit to 140 degrees Fahrenheit depending on the type of wax material. For instance, paraffin wax melts at a lower temperature, close to 100 degrees Fahrenheit, as opposed to beeswax which melts at a higher temperature of approximately 130-140 degrees Fahrenheit. Controls may be provided on the device for controlling the operational temperature of the heater 54.

As seen in FIG. 7, an arrangement of LEDs 56 may be provided near the bottom of the fan chamber 20 or another location within the interior chamber of the housing 12. In one embodiment, the LEDs may be contained on a printed circuit board 52. Upon operation to illuminate the LEDs 56, light is directed upwardly through the interior chamber of the housing, including through the transverse shelf 24 and out through the top annular ledge 30, as well as out through the cover 14 which is at least partially formed of a transparent or translucent material. Thus, activation of the LEDs 56 serves to direct light out from the top 36 of the cover 14, as well as possibly the sides of the cover. The printed circuit board 52 or other control module may be adapted to signal a change of colors of the illuminated LEDs as desired by the user. As seen in FIG. 7, the lowermost side portion of the housing 12 may be provided with vent openings 58 to allow air to enter into the fan chamber upon operation of the fan 50. This may enhance airflow upwardly through the interior chamber and out through the vented opening 40 or openings 46 in the cover 14, carrying the desired aroma of the wax material 80 being melted within the wax melt container.

Figure 13:
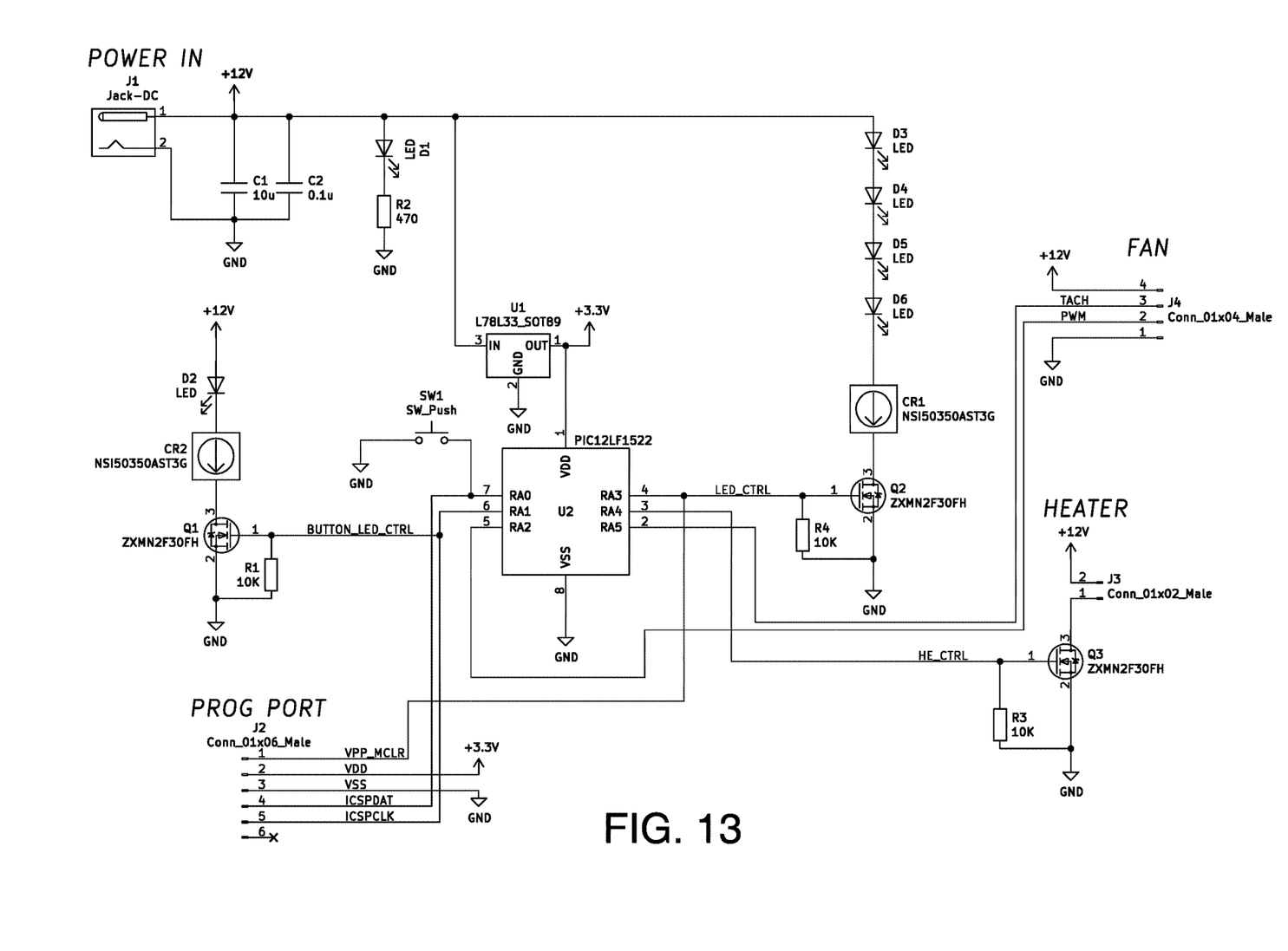
FIG. 13 is an electrical schematic diagram of the electrically powered components of the wax melt air freshener device of the present invention.
Figure 14:
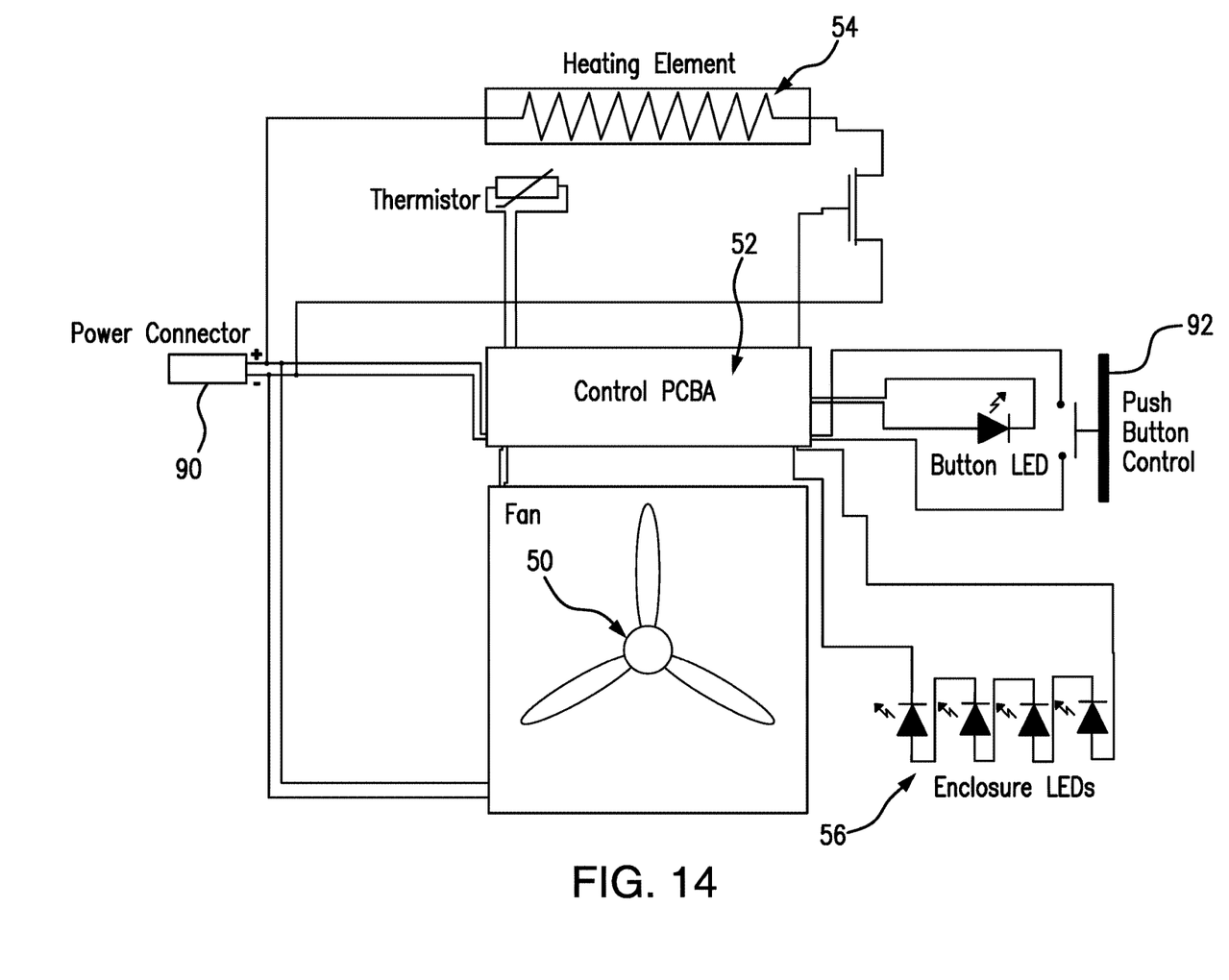
FIG. 14 is a general schematic diagram showing the primary electrical components of the wax melt air freshener device of the present invention.

The device 10 is adapted to be connected to an electric power source with the use of a power cord 90. The power cord 90 may be removable from the air freshener device 10 or, alternatively, permanently connected to the air freshener device 10. In the event the power cord 90 is removably attachable to the air freshener device 10, the connection of the power cord 90 to the air freshener device 10 can be via any known electrical connection method, including a USB connection. The opposite end of the power cord 90 may be provided with a USB plug for connection to a USB outlet in an automobile or other location. Alternatively, the opposite end of the power cord 90 may be provided with a cigarette lighter plug for electrical connection within a cigarette lighter socket in an automobile. Electric power is provided to the air freshener device through the connected power cord 90 to thereby operate the fan 50, the heater 54 and LEDs 56. A push button control 92 on the side of the housing 12 is operable to close a circuit of the device to thereby direct electric power to the fan 50, heater 54 and LEDs 56. The circuitry of the air freshener device 10, as shown in FIGS. 13 and 14, may be adapted to allow for controlling various functions of the device by depressing the button multiple times, such as changing the speed of the fan 50, increasing the temperature of the heater 54 and changing the color of light emitted from the LEDs 56.

Figure 8:
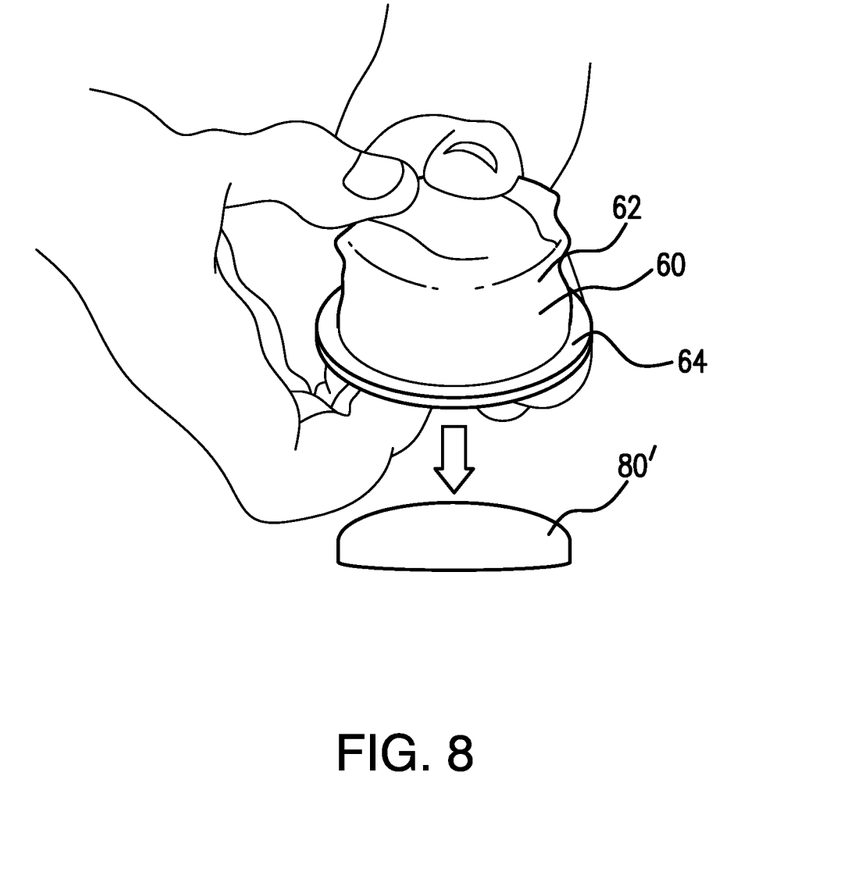
FIG. 8 is a perspective view illustrating a user removing previously melted and now hardened wax material from the wax melt container by pressing on the bottom of the wax melt container, causing the silicone bottom portion of the container to depress and release the hardened wax material from the container.

Referring to FIG. 8, the wax melt container 60 is shown, wherein at least the bottom portion of the container 60 is formed of silicone, allowing the bottom portion to be flexible and depressed inwardly to deform and push out the wax material 80' after it has melted and subsequently hardened to form the shape of the bottom of the wax melt container 60. This allows the wax material 80' to be removed and then reused again at a later time. Moreover, this allows the user to conveniently pop out the hardened wax material 80' that was previously melted, and then swap out the wax material for another wax material having a different aroma. For example, when driving in the morning, the user may desire to have a wakeup aroma that may be a stronger scent. Then, on the way home, at the end of the day, the user may want a more relaxing aroma. The silicone wax melt container 60 allows the wax material to be easily removed, so that the user can swap out different aroma wax materials in and out of the wax melt container. The silicone material also allows the wax melt container 60 to remain cool to the touch, even when containing melted wax that has been heated by the heater 54. To remove the hardened wax material 80' that was previously melted, the user simply inverts the wax melt container, as seen in FIG. 8, and presses down on the silicone bottom of the container, causing the bottom to be pushed inwardly and deform, resulting in the hardened wax material 80' popping out of the wax melt container.

Figure 9:
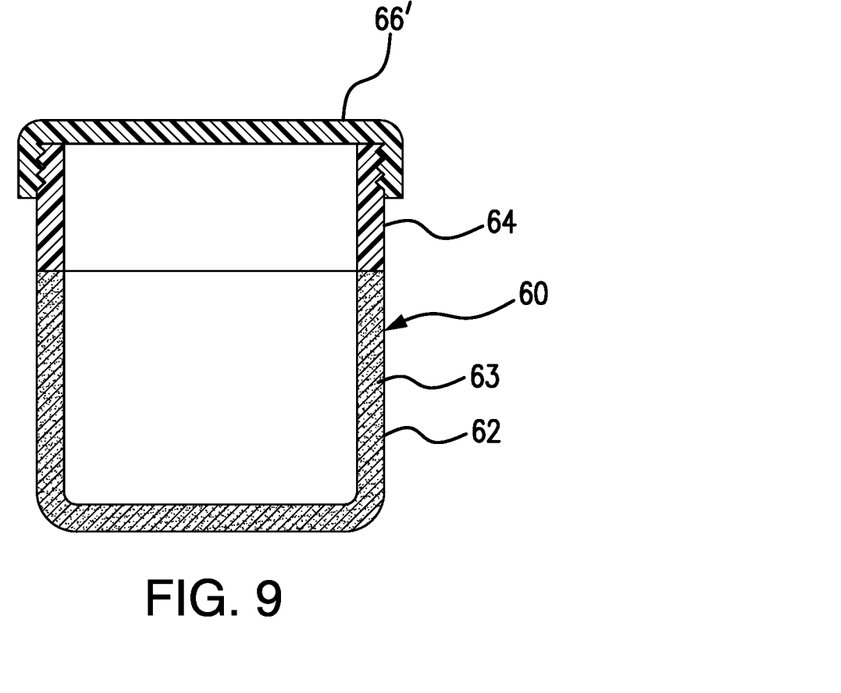
FIG. 9 is a side elevational view, shown in cross-section, illustrating one embodiment of the wax melt container of the present invention including a silicone bottom portion and a hard, plastic upper portion and removable top.
Figure 10:
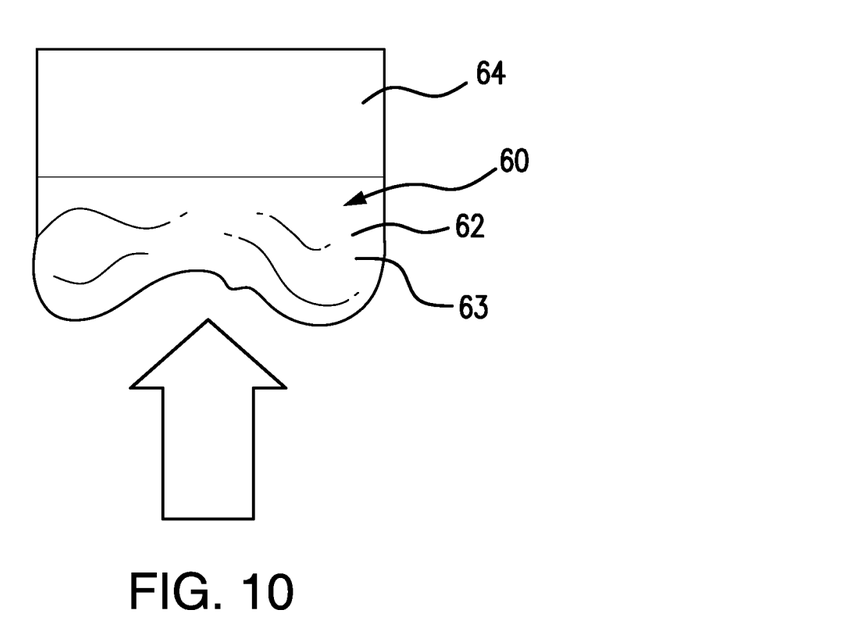
FIG. 10 is a side elevational view illustrating collapsing movement of the silicone bottom portion of the wax melt container of FIG. 9 upon application of an external force, as indicated by the arrow, to thereby release previously melted and now hardened wax from the wax melt container.

FIGS. 9 and 10 show a further embodiment of the wax melt container 60 wherein a lower portion 63 of the wax melt container is formed of silicone and an upper portion 64 is formed of a rigid material, such as a rigid plastic material. This allows the top 66' to be easily screwed onto the threaded top of the wax melt container 60, as seen in FIG. 9.

Figure 11:
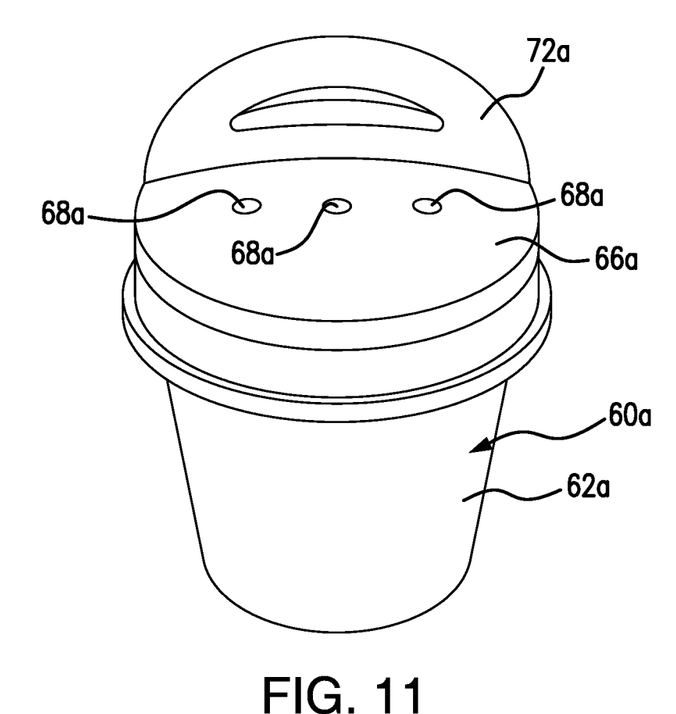
FIG. 11 is a front, top perspective view of another preferred embodiment of the wax melt container and top.
Figure 12:
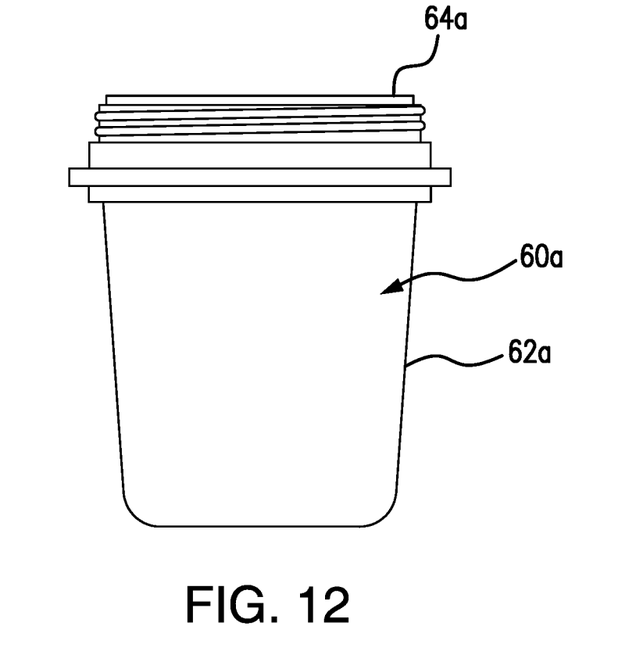
FIG. 12 is a side elevational view of the wax melt container of FIG. 11, shown with the top removed, and including a silicone wall structure and top silicone rim.

Referring to FIGS. 11 and 12, another embodiment of the wax melt container is shown and is generally indicated as 60a. In this particular embodiment, which is one preferred embodiment, the container 60 is formed of a silicone material, including the bottom and side walls 62a, as well as a top lip 64a. A rigid plastic collar is fitted around the silicone container to provide threads for attachment of the top 66a. Similar to previous embodiments, the top 66a includes vent openings 68a and a handle 72a. The handle 72a allows the wax melt container to be easily removed and replaced within the housing 12 of the air freshener device 10.

Since many modifications, variations and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An air freshener device comprising:
a main housing including an interior chamber;
a cover removably attachable to a top of the main housing, and the cover including at least one air vent;
an electrically powered heater within the interior chamber;
a wax melt container for holding a fragrant wax material therein, and the wax melt container including a bottom, an open top and a side wall structure extending from the bottom to the open top, and the wax melt container further including a removable lid for covering the open top of the wax melt container, and the removable lid including at least one vent opening, and at least the bottom of the wax melt container being formed of a flexible and resilient material that is adapted to be depressed inwardly towards an interior of the wax melt container for urging release of the fragrant wax material after melting and re-hardening;

a support structure for removably supporting the wax melt container within the interior chamber of the main housing so that at least the bottom of the wax melt container is in heat receiving relation to the electrically powered heater to cause the fragrant wax material to melt and release an aroma upwardly towards the lid and through the at least one vent opening;

an electrically powered fan within the interior chamber of the main housing for creating an upward airflow through the interior chamber and out through the at least one air vent in the cover and causing the aroma released by the melting fragrant wax material to be carried upwardly in the airflow and out through the at least one air vent in the cover; and the lid of the wax melt container having a closure mechanism for preventing the melted fragrant wax material from spilling out of the wax melt container.

2. The air freshener device as recited in claim 1 further comprising:

at least a portion of the cover including a light passage material for allowing light to pass through the at least a portion of the cover; and at least one light emitting diode within the interior chamber for generating light that passes through the at least a portion of the cover so that the light is emitted from the cover of the air freshener device.

3. The air freshener device as recited in claim 1 wherein at least the bottom of the wax melt chamber is formed of silicone.

4. The air freshener device as recited in claim 1 wherein the bottom and at least a portion of the side wall structure of the wax melt container are formed of silicone.

5. The air freshener device as recited in claim 1 wherein the bottom, the side wall structure and a top annular lip of the wax melt container are formed of silicone.

6. The air freshener device as recited in claim 2 further comprising:

a plurality of light emitting diodes in the interior chamber for generating light that passes through the at least a portion of the cover so that light is emitted from the cover of the air freshener device.

7. The air freshener device as recited in claim 1 wherein the cover is removably attachable to the top of the main housing in sealed relation therewith to prevent the melted fragrant wax from leaking between the main housing and the cover.

8. The air freshener device as recited in claim 7 wherein the at least one air vent in the cover is structured and disposed to prevent the melted fragrant wax from leaking therethrough.

9. The air freshener device as recited in claim 2 wherein the support structure for removably supporting the wax melt container is at least partially formed of a transparent material to allow passage of light from the at least one light emitting diode therethrough and upwardly to the cover.

10. The air freshener device as recited in claim 1 further comprising:

the air freshener device being structured for receiving electrical power from an electric power supply source; and a push button control on the main housing for controlling operation of the electrically powered heater and the electrically powered fan between at least an on state and an off state.

11. The air freshener device as recited in claim 2 further comprising:

the air freshener device being structured for receiving electrical power from an electric power supply source; and a push button control on the main housing for controlling operation of the electrically powered heater and the electrically powered fan, and the at least one light emitting diode between at least an on state and an off state.

* * * * *